United States Patent [19]

Daniel

[11] Plant 4,453

[45] Aug. 21, 1979

[54] DISTINCT VARIETY OF BLUEGRASS PLANT

[75] Inventor: William H. Daniel, West Lafayette, Ind.

[73] Assignee: Purdue Research Foundation, West Lafayette, Ind.

[21] Appl. No.: 905,850

[22] Filed: May 15, 1978

[51] Int. Cl.[2] ..... A01H 5/00

[52] U.S. Cl. ..... Plt./88

[58] Field of Search ..... Plt./88

*Primary Examiner*—Robert E. Bagwill
*Assistant Examiner*—James R. Feyrer
*Attorney, Agent, or Firm*—John R. Nesbitt

[57] ABSTRACT

A Kentucky bluegrass plant which exhibits strong rhizome spread and thus predominates over other adjacent bluegrasses. The plant is a medium to light green color and this contributes to more drouth tolerance than dark green bluegrasses characteristically have. The new variety has moderate leafspot and powdery mildew resistance and is ideally suited for roadside use where competition from weeds is intense. The density and wear resistance of the new variety also make it useful for athletic fields, playgrounds, parks, and other surfaces where a high wear factor is involved. The new variety of Kentucky bluegrass was developed from clones originally discovered during 1952 among a collection of 24 bluegrasses taken from fairways of the Chicago Golf Club of Wheaton, Ill., in a cultivated area. The new variety was the result of six generations as reported hereinafter, and the variety has been named "Wabash". The instant plant was asexually reproduced by cuttings through succeeding propagations. Each subsequent generation from seed maintained the characteristics of the original parent plant. The original plant was selected as a discovery which was unique. The subject plant is a single, genetically identical plant, as shown by the fact that applicants carried through additional generations and continued to find that this particular plant was genetically true. A single plant propagation was used, reproduced in series, as a way of maintaining identity. The plant increase began with 1W19N, the sixth generation. The variety is characterized by its rapid spread by rhizomes and its predominance in solid stands after establishment. Its tolerance to disease and its good density have resulted in reduction of crabgrass and weed infestation of Wabash stands when compared to other bluegrass cultivars. The new variety has greater tolerance to drouth, probably due to its lighter green color, as indicated by delayed wilting. It is distinctive in this wilt resistance from all other varieties of which applicant is aware.

6 Drawing Figures

BACKGROUND OF THE INVENTION

Figure 1:
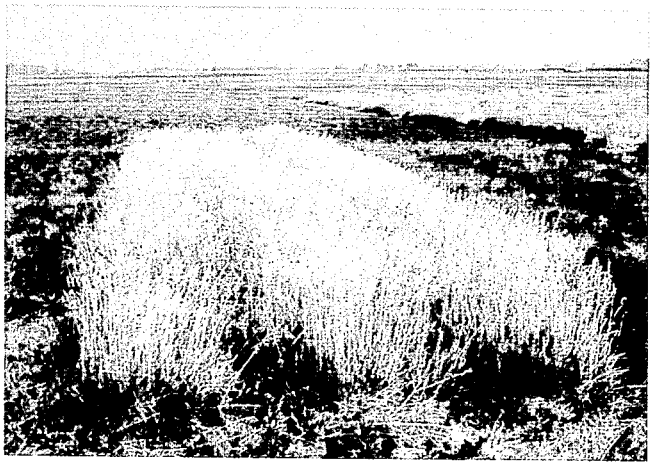
FIG. 1 is a photograph showing three rows of Wabash bluegrass nearing maturity, about 25 inches tall, second year harvest.
Figure 2:
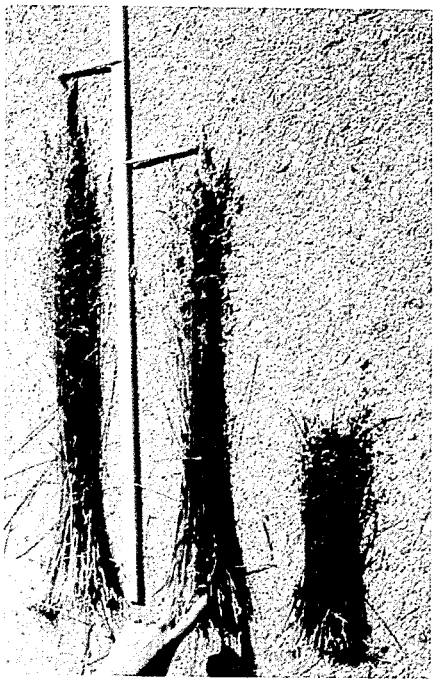
FIG. 2 is a photograph showing the Wabash variety (photo, center) in comparison with common bluegrass (photo, left) and an experimental dwarf type bluegrass (photo, right).
Figure 3:
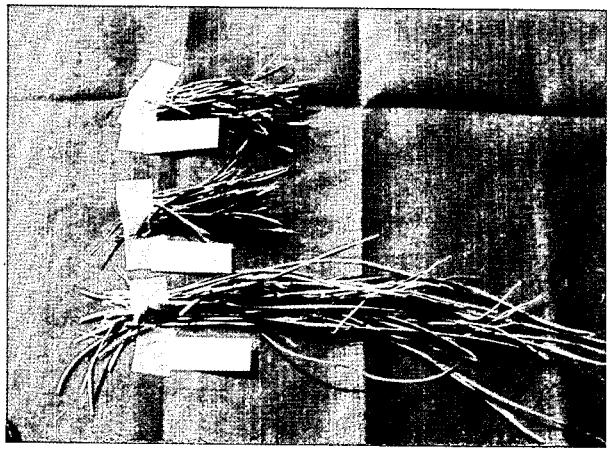
FIG. 3 is a photograph taken in August 1975 after mowing, and the excellent regrowth of Wabash (photo, top) compared with bluegrass P-104 (U.S. Plant Pat. No. 3,643) (photo, middle) and TVA, a tall common type bluegrass (photo, bottom) is shown.
Figure 4:
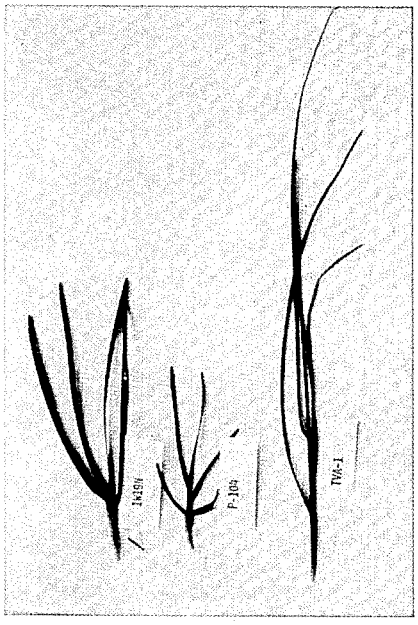
FIG. 4 is a photograph showing bluegrass tillers of the same age, and under the same management, of Wabash (photo, top), P-104 (photo, middle) and TVA (photo, bottom).
Figure 6:
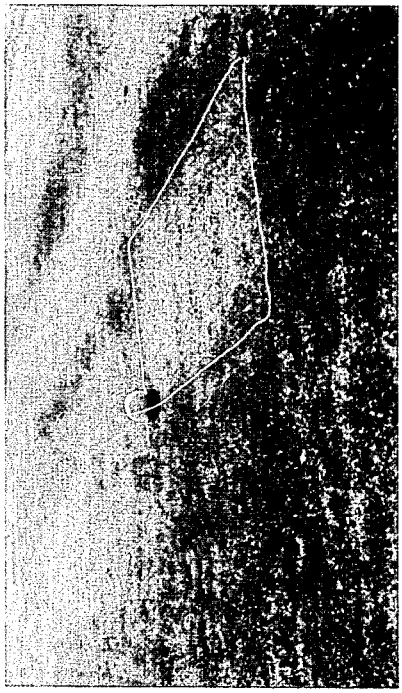
FIG. 6 is a photograph generally showing drouth tolerance of the light green Wabash bluegrass marked plot compared to the surrounding darker green plots which show wilt.
Figure 5:
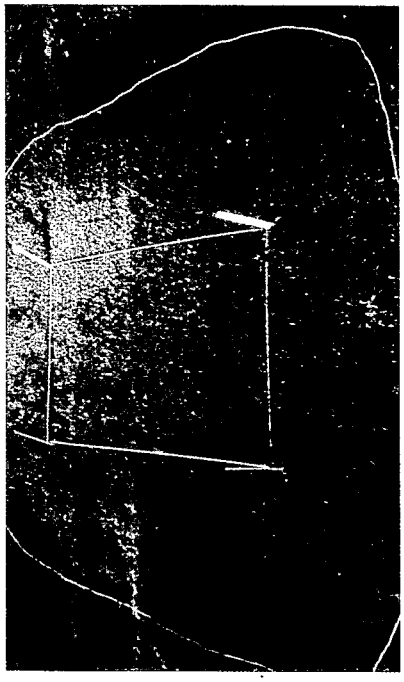
FIG. 5 is a photograph of 16B (a parent of Wabash) and the genetic rigor of the parent strain is evident in this 8 year plot showing the spread of 16B into the 8 adjacent plots.

After the original clone was selected, and assigned an identity number of 16B, six subsequent generations were selected and numbered, respectively, A8, 23-14, 1-10-1, A4, D5-8, and 1W19N, which selection maintained the same light green vigorous appearance and growth type.

The original selection made, with the most spread of all selections made at that time, was 16B, the second clone taken upon leaving the No. 16 tee area at the golf course aforesaid. Interestingly enough, Warren's Turf Nursery later made comprehensive selections from this same golf course but, upon investigation by the applicant and others, it has been established that their A-34, A-20 and A-10 bluegrasses are not from the clone discovered by applicant and furthermore, Wabash is six generations of selection away from the original clone.

Sprigs from each clone taken were vegetatively planted in 1952 in small plots within field 10B3 at the Agronomy Farm, Purdue University. When many seedlings from the seed harvested were space planted, over 100 types were selected as different. For example, five were dwarf fine leaved, yet some were very wide leaved, and since then six generations have been recorded.

These generations are as follows:

Generation 1. 16B1 — this is a selected type similar to the mother, has good spread, and was transplanted and the seed harvested.

Generation 2. A8 — seedlings were spaced into 10B3S in the fall of 1961. Row A, plant 8 was chosen as representative of the light green colored vigorous spread type being sought. Seed harvests were made in 1962, 1963, and 1964 before the plants were killed in 1965.

Generation 3. Row 23, Plant 14 in 9A3 was space planted in 1965, harvested, and then killed in 1966, and this was another typical plant chosen for the desired type.

Generation 4. Block 1, Row 10, Plant 1 in field 9A1 was space planted in 1966.

Generation 5. Row A, plot 4 included 33 seedlings space planted into 10B3C in the spring of 1969. The seed was harvested in 1970 and then the stand was mowed as turf in 1970–71 and the seed harvested again in 1972. Some seed was planted as a roadside test along U.S. Interstate Highway 65 near its intersection with Indiana State Highway 38 in the fall of 1972. Also some sod was cut off and placed in two plots at this location. Eight plugs from A-4 were transferred to Block D, Row 5, plot 8 in 9A1 in the fall of 1970. The uniform vigorous spread and medium green color was the basis for selection for seed harvest from this plot in 1972–75. These plots were killed in 1975.

Generation 6. Block 1 West 19 North was 35 seedlings spaced in field 9A3 in 1973. The seed harvested off this plot in 1974 and 1975 was transferred to the Agricultural Alumni Seed Improvement Association for increase in the early fall of 1975 and identified as the variety "Wabash". The new variety has remained true to its original type as selected for drouth resistance, light green color and aggressive rhizome spreading. The variety can be asexually reproduced, although seed production runs true to type as discussed more completely below under "Apomixis".

DETAILED DESCRIPTION OF THE NEW VARIETY

The new Wabash variety of Kentucky bluegrass possesses the following combination of characteristics:

1. An excellent spreadability as clones.
2. A medium to light green color.
3. High drouth tolerance.
4. Medium seed head height.
5. Improved leafspot resistance.
6. Stripe smut and flag smut resistance.
7. Dense penetrating turf.

The characteristics of the new variety described above are hereafter described in more detail, and it should be noted that for several years in applicant's research at Purdue University it was attempted to find a dark green, low growing type bluegrass. None was found equal to the lighter green types similar to the original parent of Wabash as described above. The original mother plant, 16B, when singular tiller starts were made, increased the most when compared to other bluegrass clones collected from the same Chicago Golf Club at other locations during 1952, the comparison is shown in the following Table 1, and the source is a thesis by Lobenstein, Table 3, on file at Purdue University, dated 1964, such data being as follows:

Table 1

| Number of Rhizomes Produced from Single Tiller | | | | | |
|---|---|---|---|---|---|
| Experiment No. | | R1 | R2b | 13b | R4b |
| Days of Growth | | 180 | 180 | 150 | 90 |
| 16B | | 333 | 230 | 393 | 103 |
| p.p. 3135 | (dwarf) | 108 | 175 | 28 | 10 |
| Range of | High | 333 | 256 | 393 | 103 |
| 16 in test: | Low | 39 | 76 | 55 | 10 |

Some data on entry A-4 (5th generation) in field from 10B3C (date from Record Book 27, page 77) give identity and comparisons.

Leaf height spring = 26 cm when range was 32-10 on 11 May 70.

Leaf height early fall = 13 cm when range was 19-7 on 26 Au 70.

Color — medium.

Leaf height — medium.

Spread — vigorous, desired.

Rust rating — 6-medium, when 1 best, 9 poorest.

Leaf spot res. — 2-very good, when 1 best, 9 poorest.

Spread May '70 — 110 cm.-fast. Turf types were only 60–70 cm.

Sod of A-4 was moved on 30 Se 70 to test plots on I-65 at Hwy. 38 as entries 3 and 7, have been mowed and maintained as roadsides since then.

The Wabash variety was also compared with other standard bluegrasses, and the data is set forth in the Lobenstein thesis above referenced, and is reproduced in the following Table 2:

Table 2

| Comparisons for Wabash and Standards | | | | | | | | | |
|---|---|---|---|---|---|---|---|---|---|
| | Height Leaves | | Spread | | of Spread Diameter | Area Covered | Leaf Ht. | Seed per | Germ Lab. |
| Seed Plot | 19 Oc 73 cm | 13 Mi 74 cm | 15 Mi 74 cm | 12 Au 74 cm | 31 De 74 cm | 31 DE 74 $m^2$ | 31 De 74 cm | Gram no. | test % |
| Wabash | 17 | 23 | 56 | 90 | 120 | 1.13 | 12 | 4700 | 92 |
| Baron | 13 | 15 | 52 | | — | — | — | — | — |
| Nugget | 16 | 10 | 40 | | — | — | — | — | — |
| RI 10 | 28 | 15 | 51 | | 70 | .38 | — | — | — |

Seedling Vigor: Seedlings planted in the greenhouse at Purdue on 9 Ja 75, were rated 5, or average, on earliness, and 1, as best on stand. In standard seed laboratory testing, germination averaged 94%, that being the best of 50 experimental bluegrasses tested. The range found under that test was 94 to 34%.

Plant Maturity: Wabash variety matured on a 5 rated, medium, wherein 1 is the latest and 9 is the earliest of all bluegrasses in the test.

In 1976 there were 7 entries earlier, 10 about equal to Wabash, and 17 later in maturity than Wabash. In 1976, some second year old seed rows averaged 64 cm. in height when AQ6 (one parent of Sodco variety) averaged 35. In field 9A3 transplants of seedlings made in June 1973 had, by 4 Se 73, spread as follows: Wabash — 40 cm.; Sodco — 30 cm. and out of 75 entries in the test the spread range was from 50 to 20 cm. When the Wabash variety was left unmowed all summer its leaf height on 3 Se 74, was 15 cm. while the range of the same 75 entries was between 25 to 5 cm.

Apomixis: Out of 70 seedlings of A4 (the 5th seedgeneration from the original 16B clone) no off-types were found. In 405 space planted seedlings in 1975 of 1–19 (the 6th generation) two off-types observed were limited to 8 lower leaved and 9 medium leaved plants. These variants were less vigorous than the 388 identical Wabash plants so would not show significantly in a seed field or turf planted with Wabash variety seed. This indicates that the variety is approximately 96% apomictic. Furthermore, field observations indicate that seed from the 1W19N generation had production equal to the seed yield of the commercially available cultivar Baron which yields approximately 1100 lbs. of seed per acre under normal conditions of seed production.

Color and Drouth Tolerance: Field plot observations from 1962 through 1975 show that as drouth starts, the lighter green bluegrasses stay turgid 1–2 days longer than the dark green selection such as Fylking, Nugget and Sodco. It is possible that the leaf with a lighter green color has a slightly lower evaporation and transpiration rate than those with the dark blue-green color, but in any event the wilt resistance of the Wabash variety is high. Wabash, located in 9A3, has been classified as a light colored highway type bluegrass in 1974 and 75; in 1976 it was rated 4, when 1 is darker green and 9 is lightest green of all plants tested. The characteristic color of the "Wabash" variety, based upon the *Universal Language & Dictionary of Names,* U.S. *Department of Commerce NBS Special Publication* 440, is moderate olive green 125, having a Munsell value of 3.5, and a Munsell Chroma 5.

What is claimed is:

1. A new and distinct variety of bluegrass plant, *Poa pratensis,* substantially as described and illustrated, and particularly characterized by a medium green color, vigorous rhizome spread, and good disease tolerance.

* * * * *